(12) United States Patent
Boogers et al.

(10) Patent No.: US 7,473,792 B2
(45) Date of Patent: Jan. 6, 2009

(54) PROCESS FOR TRANSITION METAL-CATALYZED ASYMMETRIC HYDROGENATION OF ACRYLIC ACID DERIVATIVES, AND A NOVEL CATALYST SYSTEM FOR ASYMMETRIC TRANSITION METAL CATALYSIS

(75) Inventors: Jeroen Boogers, Maastricht (NL); Ulfried Felfer, Linz (AT); Martina Kotthaus, Linz (AT); Andreas H. M. De Vries, Maastricht (NL); Johannes G. De Vries, Maastricht (NL); Laurent Lefort, Maastricht (NL); Gerhard Steinbauer, Enns (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 0 days.

(21) Appl. No.: 11/666,922

(22) PCT Filed: Dec. 5, 2005

(86) PCT No.: PCT/EP2005/012990

§ 371 (c)(1),
(2), (4) Date: May 3, 2007

(87) PCT Pub. No.: WO2006/069617

PCT Pub. Date: Jul. 6, 2006

(65) Prior Publication Data

US 2007/0293691 A1 Dec. 20, 2007

(30) Foreign Application Priority Data

Dec. 27, 2004 (AT) .............................. A 2174/2004

(51) Int. Cl.
*C07F 15/00* (2006.01)
*B01J 31/00* (2006.01)
*C07C 57/02* (2006.01)

(52) U.S. Cl. .......................... 556/13; 502/155; 562/598
(58) Field of Classification Search ................ 556/13; 502/155; 562/598
See application file for complete search history.

(56) References Cited

U.S. PATENT DOCUMENTS 5,210,243 A 5/1993 Kolich

FOREIGN PATENT DOCUMENTS

| WO | WO 02/0446 A2 | 1/2002 |
|----|----|----|
| WO | WO 02/02500 A | 1/2002 |
| WO | WO 2004/035208 A | 4/2004 |
| WO | WO 2004/035208 A1 * | 4/2004 |

OTHER PUBLICATIONS

Panetta et al., Chemical Communications, pp. 5656-5668 (2005).*
Xu et al., Organic Letters, vol. 6, No. 22, pp. 4105-4107 (2004).*
Kostas et al., Applied Organometallic Chemistry, vol. 19, pp. 1090-1095 (2005).*
Huang et al., Tetrahedron: Asymmetry, vol. 16, pp. 693-697 (2005).*
Reetz et al, "Mixtures of chiral and achiral monodentate ligands in asymmetric Rh-catalyzed olefin hydrogenation: reversal of enantioselectivity", Tetrahedron Letters, vol. 44, 2003, pp. 4593-4596.
International Search Report mailed Feb. 16, 2006 in PCT/EP2005/012990.
Written Opinion mailed Feb. 16, 2006 in PCT/EP2005/012990.

* cited by examiner

*Primary Examiner*—Porfirio Nazario Gonzalez
(74) *Attorney, Agent, or Firm*—Nixon & Vanderhye PC

(57) ABSTRACT

A process for transition metal-catalyzed, asymmetric hydrogenation of acrylic acid derivatives of the formula (I) in which R1 is H or an optionally substituted alkyl, aryl or heteroaryl radical, R2 is an optionally substituted alkyl, aryl or heteroaryl radical, and R3 is H or a $C_1$-$C_6$-alkyl radical, which comprises hydrogenating compounds of the formula (I), optionally in a solvent, in the presence of one or more hydrogen donors, using a catalyst system which comprises a transition metal from the group of ruthenium, rhodium and iridium and a combination of a chiral phosphorus ligand of the formula (II) in which Cn, together with the two oxygen atoms and the phosphorus atom, forms an optionally substituted ring having from 2 to 6 carbon atoms and R4 is an optionally substituted alkyl, aryl, alkoxy or aryloxy radical or NR5R6 where R5 and R6 may each independently be H or an optionally substituted alkyl, aryl, aralkyl or alkaryl radical, or, together with the nitrogen atom, may form a ring, and an achiral phosphine ligand of the formula (III) in which R is an optionally substituted alkyl or aryl radical, to the corresponding compounds of the formula (IV) in which R1, R2 and R3 are each as defined above, and also a novel catalyst system for asymmetric transition metal catalysis.

25 Claims, No Drawings

PROCESS FOR TRANSITION METAL-CATALYZED ASYMMETRIC HYDROGENATION OF ACRYLIC ACID DERIVATIVES, AND A NOVEL CATALYST SYSTEM FOR ASYMMETRIC TRANSITION METAL CATALYSIS

This application is the US national phase of international application PCT/EP2005/012990 filed 5 Dec. 2005 which designated the U.S. and claims benefit of AT A 2174/2004, dated 27 Dec. 2004, the entire content of which is hereby incorporated by reference.

The present invention relates to a process for transition metal-catalyzed asymmetric hydrogenation of acrylic acid derivatives, for instance alpha-substituted cinnamic acid derivatives, to the corresponding chiral acids or esters, and also a novel catalyst system with a specific ligand system consisting of a chiral phosphorus ligand and an achiral phosphine ligand for asymmetric catalysis.

Acrylic acid derivatives, for instance alpha-substituted cinnamic acid derivatives, constitute valuable intermediates for the preparation of pharmaceuticals, for instance for delta-amino-gamma-hydroxy-omega-arylalkanecarboxamides, which have renin-inhibiting properties and can be used as an antihypertensive in pharmaceutical preparations.

Catalysts, and also processes for transition metal-catalyzed asymmetric hydrogenations of unsaturated compounds, have already been described in the literature.

For example, WO 02/02500 states that the asymmetric hydrogenation of alpha, beta-unsaturated carboxylic acids with homogeneous, asymmetric hydrogenation catalysts is known per se and that specifically ruthenium and rhodium catalysts are very effective therefor. The ligands used are chiral di-tertiary diphosphines. With these systems, it is possible according to WO 02/02500 to attain optical yields of up to 80% ee. As an improvement to these catalysts, WO 02/02500 proposes the use of a bidentate ligand with a ferrocenyl basic structure.

Adv. Synth. Catal. 2003, 345, p. 160-164 discloses further diphosphine ligands based on a ferrocenyl-aryl basic structure, known as the walphos ligand family, which are used in the rhodium- or ruthenium-catalyzed asymmetric hydrogenation of olefins and ketones. The walphos ligands are used in combination with a ruthenium or a rhodium source, for instance Ru(methylallyl)$_2$COD, [(NBD)$_2$Rh]BF$_4$ or [(COD)$_2$Rh]BF$_4$, for example for the hydrogenation of cinnamic acid derivatives, in which optical purities of up to 95% ee are achieved.

A disadvantage in this process is in particular the high costs of the walphos ligand, since the synthesis of the ligand is distinctly more complicated.

WO 02/04466 discloses further catalysts which have a monodentate ligand. However, it has been found that the monophos catalyst systems described therein are less active for cinnamic acid derivatives in particular, as a result of which longer hydrogenation times are required, and lead to poorer enantiomeric excesses.

WO 2004/035208 describes mixtures of monophosphorus compounds as ligand systems for asymmetric transition metal catalysis. It is known from Example 8 of the application that a mixture of chiral phosphonite or phosphite ligands and an achiral monophosphorus ligand leads to distinctly poorer results with regard to optical purity than when a mixture of chiral monophosphorus compounds is used.

Since there is still a great need for improved processes with improved catalyst systems in the field of asymmetric hydrogenation of acrylic acid derivatives, it is an object of the present invention to find a process for transition metal-catalyzed asymmetric hydrogenation of acrylic acid derivatives, and also a novel catalyst system which enables, in a simple, inexpensive manner, the preparation of the desired compounds in optical purities, higher compared to the prior art, of up to 100% ee, and in higher yields of up to 100% of theory.

The present invention accordingly provides a process for transition metal-catalyzed, asymmetric hydrogenation of acrylic acid derivatives of the formula (I)

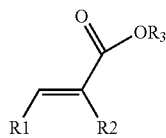

in which R1 is H or an optionally substituted $C_1$-$C_{20}$-alkyl, $C_5$-$C_{20}$-aryl or $C_5$-$C_{20}$-heteroaryl radical, R2 is an optionally substituted $C_1$-$C_{20}$-alkyl, $C_5$-$C_{20}$-aryl or $C_5$-$C_{20}$-heteroaryl radical, and R3 is H or a $C_1$-$C_6$-alkyl radical, which comprises hydrogenating compounds of the formula (I), optionally in a solvent, in the presence of one or more H donors, using a catalyst system which comprises a transition metal from the group of ruthenium, rhodium and iridium and a combination of a chiral phosphorus ligand of the formula (II)

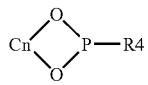

in which Cn, together with the two oxygen atoms and the phosphorus atom, forms an optionally substituted ring having from 2 to 6 carbon atoms and R4 is an optionally substituted alkyl, aryl, alkoxy or aryloxy radical or NR5R6 where R5 and R6 may each independently be H or an optionally substituted alkyl, aryl, aralkyl or alkaryl radical, or, together with the nitrogen atom, may form a ring, and an achiral phosphine ligand of the formula (III)

P(R)$_3$ in which R is an optionally substituted alkyl or aryl radical, to the corresponding compounds of the formula

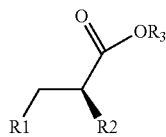

in which R1, R2 and R3 are each as defined above.

The substrates used are acrylic acid derivatives of the formula (I) in which R1 is H or an optionally substituted $C_1$-$C_{20}$-alkyl radical or an optionally substituted $C_5$-$C_{20}$-aryl or $C_5$-$C_{20}$-heteroaryl radical, and R2 is an optionally substituted $C_1$-$C_{20}$-alkyl radical or an optionally substituted $C_5$-$C_{20}$-aryl or $C_5$-$C_{20}$-heteroaryl radical.

Alkyl radicals should be understood to mean linear, branched or cyclic alkyl radicals having from 1 to 20 carbon atoms, where the alkyl chain may optionally contain one or more double or triple bonds or may be interrupted by one or more heteroatoms from the group of N, O and S.

Examples of alkyl radicals are methyl, ethyl, n-propyl, i-propyl, propenyl, n-butyl, t-butyl, cyclopentyl, butynyl, n-hexyl, cyclohexyl, i-octyl, undecyl, neoheptyl, pentadecyl, tetrahydropyrrolyl, tetrahydrofuranyl, dimethyl sulfide, etc.

Preference is given to linear, branched or cyclic alkyl radicals having from 1 to 12 carbon atoms, where the alkyl chain may optionally have a double or triple bond and may optionally contain a heteroatom.

Aryl and heteroaryl radicals are aromatic radicals having from 5 to 20 carbon atoms, for instance cyclopentadienyl, phenyl, biphenylyl, indenyl, naphthyl, pyrrolyl, furanyl, indolyl, pyrridinyl, etc. Preference is given to phenyl or naphthyl.

The radicals may be mono- or polysubstituted by suitable substituents.

Suitable substituents are, for example, $C_1$-$C_{20}$-alkoxy groups, preferably $C_1$-$C_{12}$-alkoxy groups, $C_1$-$C_{20}$-alkyl groups, preferably $C_1$-$C_6$-alkyl, $C_6$-$C_{20}$-aryl groups, preferably phenyl, trifluoro-$C_1$-$C_6$-alkyl, preferably trifluoromethyl, poly-$C_1$-$C_{20}$-alkoxy groups, halogen, for instance F, Cl, Br or I, hydroxyl, amines, nitro, nitrile, carboxylic acids, carboxylic esters or carboxamides, etc.

Particularly preferred substituents are $C_1$-$C_6$-alkoxy groups, $C_1$-$C_6$-alkyl groups, trifluoromethyl, poly-$C_1$-$C_6$-alkoxy groups, F, Cl or Br.

R3 is either H or a $C_1$-$C_6$-alkyl radical.

Particularly preferred substrates are those compounds of the formula (I) in which R2 is phenyl or a $C_1$-$C_6$-alkyl group, and R1 is an optionally mono- or polysubstituted phenyl radical, and R3 is H.

The process according to the invention for transition metal-catalyzed asymmetric hydrogenation of acrylic acid derivatives of the formula (I) proceeds in the presence of one or more hydrogen donors. In this context, hydrogen donors should be understood to mean compounds which are capable of transferring H to the substrate, for instance $H_2$, aliphatic or aromatic $C_1$-$C_{10}$ alcohols, for instance i-propanol or cyclohexanol, unsaturated hydrocarbons having 5-10 carbon atoms, for instance 1,4-dihydrobenzene or hydroquinone, or a mixture of formic acid and triethylamine, etc. (see WO 02/04466).

In some cases, for example in the case of use of an alcohol or of a hydrocarbon, the hydrogen donor can also serve as a solvent, so that no additional solvent has to be used.

Preference is given to using $H_2$ as the hydrogen donor. The hydrogen pressure in the process according to the invention is from 1 to 200 bar, preferably from 10 to 150 bar and more preferably from 15 to 100 bar.

The reaction temperature is between −20° C. and +120° C., preferably from 0 to 80° C. and more preferably from 20 to 65° C.

The asymmetric hydrogenation is preferably effected with exclusion of oxygen.

The process according to the invention is optionally carried out in a solvent.

Suitable solvents are preferably organic solvents, for example alcohols, esters, amides, ethers, ketones, aromatic hydrocarbons and halogenated hydrocarbons. Particular preference is given to using protic solvents.

Examples of preferred solvents are ethyl acetate, methanol, i-propanol, acetone, tetrahydrofuran, dichloromethane, toluene or dibromoethane.

If desired, it is also possible to use a mixture of one or more of the solvents listed above with water. The volume ratio of solvents to water is then preferably from 2:1 to 8:1, more preferably from 3:1 to 6:1.

Preference is given to a mixture of one or more protic solvents with water, as a result of which a distinct increase in the enantiomeric purity can be achieved.

The solvent used in the process according to the invention is more preferably a mixture of i-propanol and water.

The catalyst used in accordance with the invention is a catalyst system which comprises a transition metal from the group of ruthenium, rhodium and iridium, and a combination of a chiral phosphorus ligand of the formula (II) and an achiral phosphine ligand of the formula (III).

The transition metal used is preferably ruthenium or rhodium, more preferably rhodium.

Chiral ligands of the formula (II) are known and are described, for example, in WO 02/04466 or WO 2004/035208.

In the formula (II), the alkyl, aryl, alkoxy, aryloxy, aralkyl or alkaryl groups preferably have 1-20 carbon atoms and may optionally be substituted by one or more substituents from the group of hydroxyl, alkyl, alkoxy, phenyl, nitrile, carboxylic ester or halogen.

R4 in the formula (II) is more preferably an optionally substituted, linear, branched or cyclic $C_1$-$C_8$-alkyl radical, an optionally substituted phenyl radical, an optionally substituted $C_1$-$C_8$-alkoxy radical, an optionally substituted phenyloxy radical or an NR5R6 group in which R5 and R6 are preferably each independently an optionally phenyl-substituted alkyl group having 1-6 carbon atoms, more preferably having 1-3 carbon atoms, or, together with the nitrogen atom, form a ring which may optionally also contain a heteroatom, for instance O, N or S, for instance a morpholine ring, piperidine ring, pyrrolidine ring, etc. More preferably, R5 and R6 with the nitrogen atom form a 5-membered or 6-membered ring which may optionally also contain a heteroatom.

Cn is preferably a chiral, substituted $C_4$ chain (chain with 4 optionally substituted carbon atoms) with predominantly one configuration, for example with an enantiomeric excess greater than 95% ee, preferably above 99% ee.

Cn together with the two oxygen atoms and the phosphorus atom more preferably forms a 7-membered ring having 4 carbon atoms, in which case two carbon atoms in each case are part of an optionally substituted aryl group.

The aryl group is more preferably an optionally substituted phenyl or naphthyl group. The substituents are preferably attached in the o positions.

Examples of preferred chiral ligands of the formula (II) are compounds of the formula (IIa) and (IIb)

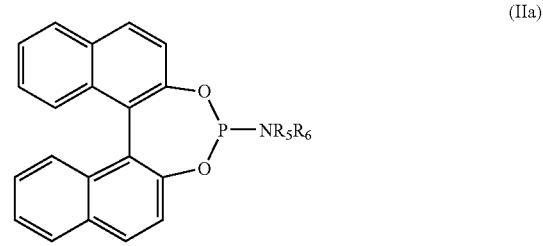

-continued

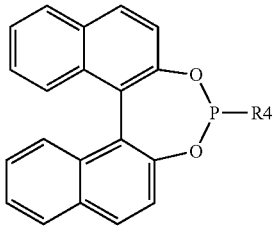
(IIb)

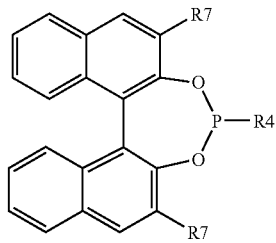
(IIf)

where the naphthyl groups are optionally mono- or polysubstituted by halogen, for instance chlorine or bromine, alkyl, preferably $C_1$-$C_6$-alkyl, or alkoxy, preferably $C_1$-$C_6$-alkoxy, aryl, preferably phenyl, aryloxy, preferably phenyloxy, R4 is an optionally substituted $C_1$-$C_6$-alkyl radical, an optionally substituted phenyl radical, an optionally phenyl-substituted $C_1$-$C_8$-alkoxy radical or an optionally $C_1$-$C_6$-alkyl-substituted phenyloxy radical, and R5 and R6 are each independently an optionally phenyl-substituted alkyl group having 1-6 carbon atoms, more preferably having 1-3 carbon atoms, or, together with the nitrogen atom, form a ring.

Further preferred chiral ligands of the formula (II) are compounds of the formula (IIc) and (IId)

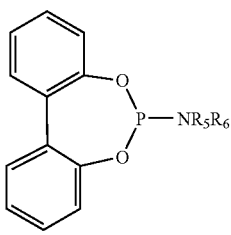 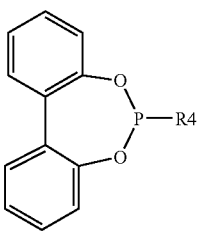

where the phenyl groups are optionally mono- or polysubstituted by halogen, for instance chlorine or bromine, alkyl, preferably $C_1$-$C_6$-alkyl, or alkoxy, preferably $C_1$-$C_6$-alkoxy, aryl, preferably phenyl, aryloxy, preferably phenyloxy, R4 is an optionally substituted $C_1$-$C_6$-alkyl radical, an optionally substituted phenyl radical, an optionally phenyl-substituted $C_1$-$C_8$-alkoxy radical or an optionally $C_1$-$C_6$-alkyl-substituted phenyloxy radical, and R5 and R6 are each independently an optionally phenyl-substituted alkyl group having 1-6 carbon atoms, more preferably having 1-3 carbon atoms, or, together with the nitrogen atom, form a ring.

Particularly preferred chiral ligands of the formula (II) are compounds of the formula (IIe) and (IIf)

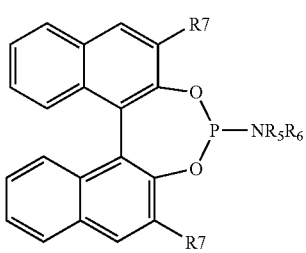
(IIe)

in which R4 is an optionally substituted $C_1$-$C_6$-alkyl radical, an optionally substituted phenyl radical, an optionally phenyl-substituted $C_1$-$C_6$-alkoxy radical or an optionally $C_1$-$C_6$-alkyl-substituted phenyloxy radical, R5 and R6 are each independently a $C_1$-$C_6$-alkyl group or, together with the nitrogen atom, form a 5-membered or 6-membered ring which may optionally also contain an oxygen or sulfur atom, and R7 a linear or branched $C_1$-$C_6$-alkyl radical, an optionally substituted phenyl radical, an optionally phenyl-substituted $C_1$-$C_6$-alkoxy radical, or an optionally $C_1$-$C_6$-alkyl-substituted phenyloxy radical.

Further particularly preferred chiral ligands of the formula (II) are compounds of the formula (IIg) and (IIh)

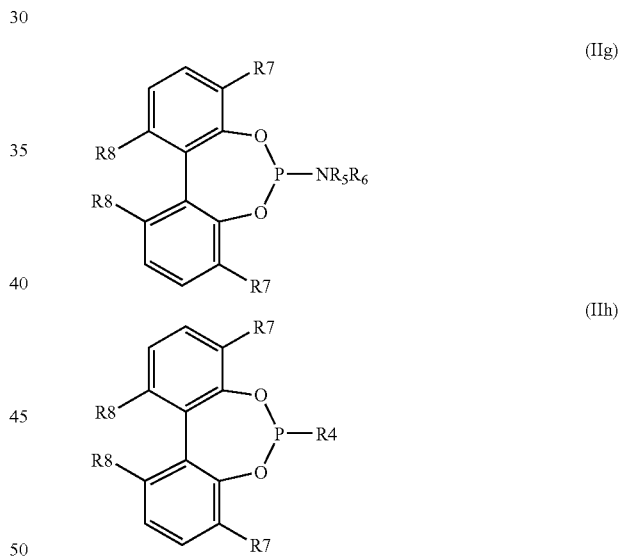

(IIg)

(IIh)

in which R4 is an optionally substituted $C_1$-$C_6$-alkyl radical, an optionally substituted phenyl radical, an optionally phenyl-substituted $C_1$-$C_4$-alkoxy radical or an optionally $C_1$-$C_6$-alkyl-substituted phenyloxy radical, R5 and R6 are each independently a $C_1$-$C_6$-alkyl group or, together with the nitrogen atom, form a 5-membered or 6-membered ring which may optionally also contain an oxygen or sulfur atom, and R7 and R8 are each a linear or branched $C_1$-$C_6$-alkyl radical, an optionally substituted phenyl radical, an optionally phenyl-substituted $C_1$-$C_6$-alkoxy radical, or an optionally $C_1$-$C_6$-alkyl-substituted phenyloxy radical.

The chiral ligands are used with an enantiomeric purity of at least 50% ee, preferably of at least 90% ee and more preferably of above 99% ee.

As a second ligand, the catalyst system used in accordance with the invention comprises an achiral phosphine ligand of the formula (III) $P(R)_3$ in which R is an optionally substituted alkyl or aryl radical.

R is preferably a linear, branched or cyclic alkyl radical having from 2 to 10 carbon atoms, more preferably having from 4 to 6 carbon atoms, or a phenyl radical optionally mono- or polysubstituted by halogen or $C_1$-$C_2$-alkyl.

Particularly preferred radicals are phenyl, o-tolyl, m-tolyl, p-tolyl, xylyl, m-chlorophenyl, p-chlorophenyl, o-methoxyphenyl, p-methoxyphenyl, m-methoxyphenyl, mesityl, cyclohexyl, n-butyl and t-butyl.

The ratio of chiral ligand of the formula (II) to achiral ligand of the formula (III) in the process according to the invention is from 10:1 to 1:5, preferably from 5:1 to 1:2, more preferably from 2.5:1 to 1.2:1.

The inventive catalyst system can be prepared analogously to WO 02/04466.

Preference is given to reacting the chiral ligand and the achiral ligand with a catalyst precursor comprising the transition metal.

Examples of suitable catalyst precursors are (COD=1,5-cyclooctadiene, NBD=norbornadiene) $[Rh(COD)_2Cl]_2$, $[Rh(COD)_2]BF_4$, $[Rh(NBD)_2]BF_4$, $Ru(OAc)_3$, $Ru(methylallyl)_2$ COD, $[Ru(cymene)Cl_2]_2$, etc.

The molar ratio of transition metal catalyst:chiral ligand is from 1:0.5 to 1:5, preferably from 1:1 to 1:2.

The molar ratio of reactant:transition metal catalyst is from 100:1 to 1 000 000:1, preferably from 1000:1 to 10 000:1.

In the process according to the invention, for example, the substrate of the formula (I), the ligands of the formulae (II) and (III), and the precursor which comprises the transition metal are dissolved in the solvent in a suitable apparatus, for instance in an autoclave. Then, the apparatus is preferably purged with inert gas, for example with $N_2$, if the exclusion of oxygen is desired. Then, the mixture is heated to the desired reaction temperature. However, preferably only the substrate is dissolved first in the solvent, then the apparatus is purged, preferably with inert gas. After heating to the appropriate reaction temperature, a suspension of the ligands of the formula (II) and (III) in degassed solvent and also the precursor which comprises the transition metal are then charged to the substrate solution.

Afterward, the hydrogen donor is added at the appropriate reaction temperature. Preference is given to injecting $H_2$ to the desired pressure. After the reaction has ended and the reaction solution has optionally been cooled, the desired end product is isolated by customary methods depending on the state of matter.

It is also possible first to prepare the catalyst complex, for example by reacting the ligands (II) and (III) with a precursor in a degassed solvent at room temperature, by stirring the reaction mixture for a certain time. Subsequently, the volatile compounds are distilled off to obtain a solid catalyst complex which is then added to the substrate solution.

The process according to the invention and in particular the use of the specific catalyst system make it possible to hydrogenate the acrylic acid derivatives firstly in a substantially less expensive manner compared to the prior art and secondly in distinctly higher enantioselectively, as a result of which the end products have a distinctly higher optical purity.

The present invention further provides a catalyst system for asymmetric transition metal catalysis, which comprises a transition metal from group VIII, IX or X and a combination of a chiral phosphorus ligand of the formula (IIa), (IIb), (IIc) or (IId) and an achiral phosphine ligand of the formula (III)

$P(R)_3$ in which R is an optionally substituted alkyl or aryl radical.

The inventive catalyst system is suitable for asymmetric transition metal catalysis, in particular for transition metal-catalyzed asymmetric hydrogenation of unsaturated compounds.

The ratio of chiral ligand of the formulae (IIa)-(IId) to achiral ligand of the formula (III) may in this case be from 10:1 to 1:5.

The ratio is preferably from 5:1 to 1:2, more preferably from 2.5:1 to 1.2:1.

Suitable transition metals are elements of groups VIII, IX or X; preference is given to using ruthenium, rhodium or iridium.

The invention further provides for the use of the inventive catalyst system for the transition metal-catalyzed asymmetric hydrogenation of unsaturated compounds.

EXAMPLE 1

Preparation of (R)-5-methoxy-3-(3-methoxypropoxy)-α-(1-methylethyl)phenylpropanoic acid In a 450 ml autoclave, 50 g (178.35 mmol) of E-2-[[4-methoxy-3-(3-methoxypropoxy)phenyl]methylene]-3-methylbutanoic acid, 100 mg (0.234 mmol) of ligand of the formula (IIe) (% ee>95%) (2,6-dimethyl-3,5-dioxa-4-phosphacyclohepta[2,1-a; 3,4-a']dinaphthalen-4-yl)piperidine, 47.6 mg (0.1172 mmol) of $Rh(COD)_2BF_4$ and 30.8 mg (0.117 mmol) of triphenylphosphine were suspended in 160 ml of isopropanol (IPA):$H_2O$=4:1. The autoclave was purged 5× with $N_2$ and heated to 55° C. Afterward, it was purged 3× with $H_2$ and subsequently pressurized to 80 bar of $H_2$ without stirring. At 80 bar/55° C. and 100 rpm of the stirrer, the mixture was then hydrogenated overnight. After 18 h, the autoclave was cooled and the desired product was isolated.

Yield: 50.35 g (96.6% of theory)
Optical purity: 95.3% ee

EXAMPLES 2-8

Analogously to Example 1, alpha-methylcinnamic acid was hydrogenated.

The reaction parameters were selected as follows: 1 mmol of substrate, reaction temperature 30° C.; 25 bar of $H_2$; 4 ml of solvent IPA:$H_2O$=4:1, reaction time 16 h; 0.01 mmol of $Rh(COD)_2BF_4$, 0.02 mmol of chiral ligand as in Example 1, 0.01 mmol of achiral ligand $P(R)_3$; see Table 1 for R.

TABLE 1

| Ex.: | R | % ee |
|---|---|---|
| 2 | phenyl | 88 |
| 3 | o-tolyl | 97 |
| 4 | m-tolyl | 87 |
| 5 | xylyl | 89 |
| 6 | m-chlorophenyl | 89 |
| 7 | p-chlorophenyl | 90 |
| 8 | cyclohexyl | 87 |

In all examples, 100% conversion was attained.

EXAMPLES 9-13

Analogously to Example 1, substituted acrylic acid derivatives of the formula

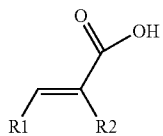

were hydrogenated. The particular definition of the R1 and R2 radicals is shown in Table 2.

The reaction parameters were selected as follows: 1 mmol of substrate, reaction temperature 30° C.; 25 bar of $H_2$; 4 ml of solvent IPA:$H_2O$=4:1, reaction time 16 h; 0.01 mmol of Rh(COD)$_2$BF$_4$, 0.02 mmol of chiral ligand as in Example 1 except that the ring in some cases contains an oxygen atom (see Table 2), 0.01 mmol of achiral ligand P(R)$_3$; see Table 2 for R.

TABLE 2

| Ex.: | R1 | R2 | R | Ring | % ee[a] |
|---|---|---|---|---|---|
| 9 | methyl | methyl | phenyl | O | 87 |
| 10 | phenyl | i-propyl | o-tolyl | $CH_2$ | 99[b] |
| 11 | 3,4-MeOPh | i-propyl | phenyl | $CH_2$ | 92 |
| 12 | 4-$CF_3$Ph | i-propyl | m-tolyl | $CH_2$ | 95 |
| 13* | phenyl | phenyl | o-tolyl | $CH_2$ | 95 |

*Example 13 was carried out at 60° C.
[a]All examples with 100% conversion expect
[b]98% conversion

COMPARATIVE EXAMPLES

Analogously to Examples 2-8, alpha-methylcinnamic acid was hydrogenated. For comparison, hydrogenation was effected in each case once with use of an inventive ligand system consisting of the combination of chiral ligand and achiral ligand PPh$_3$ and once only with use of a chiral ligand (without achiral ligand).

The reaction parameters were selected as follows: 1 mmol of substrate, reaction temperature 60° C.; 25 bar of $H_2$; 4 ml of solvent IPA, reaction time 5 h; 0.01 mmol of Rh(COD)$_2$BF$_4$, 0.02 mmol of chiral ligand of the following formula, and in some cases 0.01 mmol of achiral ligand P(Ph)$_3$.

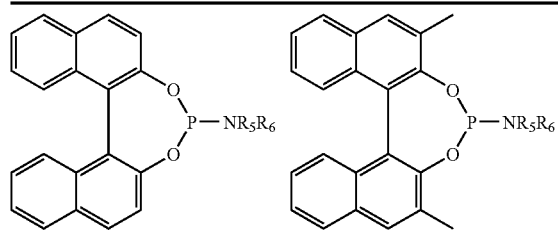

L1a: NR5R6 = NMe$_2$
L1b: NR5R6 = morpholine
L1c: NR5R6 = piperidine
L1d: NR5R6 = (R)-α-methylbenzyl-amine L2a: NR5R6 = NMe$_2$
L2b: NR5R6 = morpholine
L2c: NR5R6 = piperidine
L2d: NR5R6 = pyrrolidine

TABLE 3

| Comparative experiment | Ligand | Conversion (%) | ee (%) |
|---|---|---|---|
| 1 | L1a | 43 | 8 |
| 2 | L1a + PPh$_3$ | 100 | 43 |
| 3 | L1b | 72 | 0 |
| 4 | L1b + PPh$_3$ | 100 | 55 |
| 5 | L1c | 76 | 0 |
| 6 | L1c + PPh$_3$ | 100 | 63 |
| 7 | L1d | 91 | 0 |
| 8 | L1d + PPh$_3$ | 100 | 37 |
| 9 | L2a | 91 | 10 |
| 10 | L2a + PPh$_3$ | 100 | 80 |
| 11 | L2b | 82 | 3 |
| 12 | L2b + PPh$_3$ | 100 | 80 |
| 13 | L2c | 81 | 2 |
| 14 | L2c + PPh$_3$ | 100 | 85 |
| 15 | L2d | 86 | 16 |
| 16 | L2d + PPh$_3$ | 100 | 76 |

What is claimed is:

1. A process for transition metal-catalyzed asymmetric hydrogenation of acrylic acid derivatives of the formula (I)

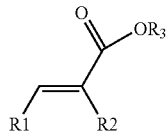

in which R1 is H or an optionally substituted $C_1$-$C_{20}$-alkyl, $C_5$-$C_{20}$-aryl or $C_5$-$C_{20}$-heteroaryl radical, R2 is an optionally substituted $C_1$-$C_{20}$-alkyl, $C_5$-$C_{20}$-aryl or $C_5$-$C_{20}$-heteroaryl radical, and R3 is H or a $C_1$-$C_6$-alkyl radical, which comprises hydrogenating compounds of the formula (I), optionally in a solvent, in the presence of one or more hydrogen donors, using a catalyst system which comprises a transition metal from the group of ruthenium, rhodium and iridium and a combination of a chiral phosphorus ligand of the formula (II)

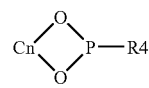

in which Cn, together with the two oxygen atoms and the phosphorus atom, forms an optionally substituted ring having from 2 to 6 carbon atoms and R4 is an optionally substituted alkyl, aryl, alkoxy or aryloxy radical or NR5R6 where R5 and R6 may each independently be H or an optionally substituted alkyl, aryl, aralkyl or alkaryl radical, or, together with the nitrogen atom, may form a ring, and an achiral phosphine ligand of the formula (III)

P(R)$_3$ in which R is an optionally substituted alkyl or aryl radical, to the corresponding compounds of the formula (IV)

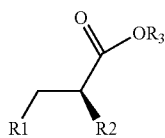

in which R1, R2 and R3 are each as defined above.

2. The process as claimed in claim 1, wherein suitable hydrogen donors act as solvents or the solvents used are alcohols, esters, amides, ethers, ketones, aromatic hydrocarbons and halogenated hydrocarbons, optionally in combination with water.

3. The process as claimed in claim 2, wherein the solvents are used in combination with water, the volume ratio of solvent to water being from 2:1 to 8:1.

4. The process as claimed in claim 3, wherein the solvent used is a mixture of 2-propanol and water in a volume ratio of from 3:1 to 6:1.

5. The process as claimed in claim 1, wherein the hydrogen donor used is $H_2$.

6. The process as claimed in claim 1, wherein the reaction temperature is between $-20°$ C. and $+120°$ C.

7. The process as claimed in claim 1, wherein the chiral ligand is used with an enantiomeric purity of at least 90% ee.

8. The process as claimed in claim 1, wherein the transition metal used is ruthenium or rhodium.

9. The process as claimed in claim 1, wherein chiral ligands of the formula (II) are used in which R4 is an optionally substituted, linear, branched or cyclic $C_1$-$C_8$-alkyl radical, an optionally substituted phenyl radical, an optionally substituted $C_1$-$C_8$-alkoxy radical, an optionally substituted phenyloxy radical or an NR5R6 group where R5 and R6 are each independently an optionally phenyl-substituted alkyl group having 1-6 carbon atoms or, together with the nitrogen atom, form a ring which may optionally also contain a heteroatom.

10. The process as claimed in claim 1, wherein chiral ligands of the formula (IIa), (IIb), (IIc) or (IId)

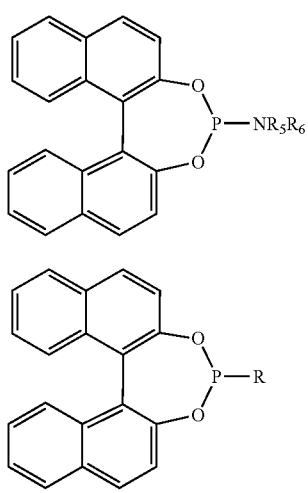

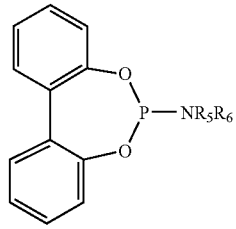

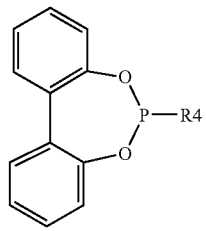

where the naphthyl and the phenyl groups may optionally be mono- or polysubstituted by halogen, alkyl, alkoxy, aryl or aryloxy, R4 is an optionally substituted $C_1$-$C_6$-alkyl radical, an optionally substituted phenyl radical, an optionally phenyl-substituted $C_1$-$C_8$-alkoxy radical or an optionally $C_1$-$C_6$-alkyl-substituted phenyloxy radical, and R5 and R6 are each independently a phenyl-substituted alkyl group having 1-6 carbon atoms or, together with the nitrogen atom, form a ring are used.

11. The process as claimed in claim 1, wherein chiral ligands of the formula (IIe), (IIf), (IIg) or (IIh)

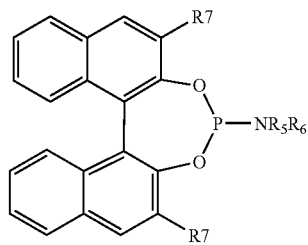

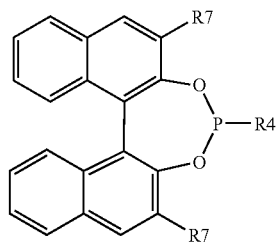

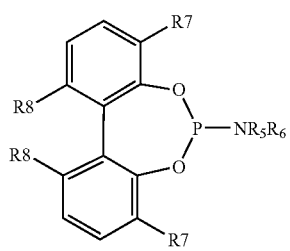

-continued

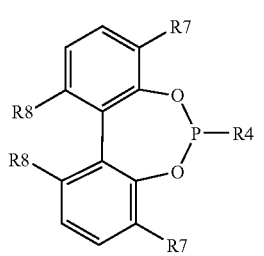
(IIh)

in which R4 is an optionally substituted $C_1$-$C_6$-alkyl radical, an optionally substituted phenyl radical, an optionally phenyl-substituted $C_1$-$C_6$-alkoxy radical or an optionally $C_1$-$C_6$-alkyl-substituted phenyloxy radical, R5 and R6 are each independently a $C_1$-$C_6$-alkyl group or, together with the nitrogen atom, form a 5-membered or 6-membered ring which may optionally also contain an oxygen or sulfur atom, and R7 and R8 are each a linear or branched $C_1$-$C_6$-alkyl radical, an optionally substituted phenyl radical, an optionally phenyl-substituted $C_1$-$C_6$-alkoxy radical, or an optionally $C_1$-$C_6$-alkyl-substituted phenyloxy radical are used, 12. The process as claimed in claim 1, wherein achiral ligands of the formula (III) are used in which R is a linear, branched or cyclic alkyl radical having from 2 to 10 carbon atoms or a phenyl radical optionally mono- or polysubstituted by halogen or $C_1$-$C_2$-alkyl.

13. The process as claimed in claim 1, wherein the ratio of chiral ligand of the formula (II) to achiral ligand of the formula (III) is from 10:1 to 1:5.

14. The process as claimed in claim 1, wherein the molar ratio of transition metal catalyst to chiral ligand of the formula (II) is from 1:0.5 to 1:5.

15. The process as claimed in claim 1, wherein the transition metal is used in the form of a catalyst precursor.

16. The process as claimed in claim 1, wherein the substrate of the formula (I), the ligands of the formulae (II) and (III), and the precursor which comprises the transition metal are first dissolved in the solvent in a suitable apparatus, then the apparatus is optionally purged with inert gas and then heated to the desired reaction temperature, or only the substrate of the formula (I) is first dissolved in the solvent, then the apparatus is optionally purged with inert gas, and only after heating to the appropriate reaction temperature is a suspension of the ligands of the formula (II) and (III) in degassed solvent and also the precursor which comprises the transition metal charged to the substrate solution, and then, in both cases, the hydrogen donor is added at the appropriate reaction temperature.

17. A catalyst system for asymmetric transition metal catalysis, which comprises a transition metal from group VIII, IX or X and a combination of a chiral phosphorus ligand and an achiral phosphine ligand, wherein the achiral phosphine ligand of the formula (III)

P(R)$_3$ in which R is optionally substituted alkyl or aryl radical, and wherein the chiral phosphorus ligands of the formula (IIe), (IIf), (IIg) or (IIh)

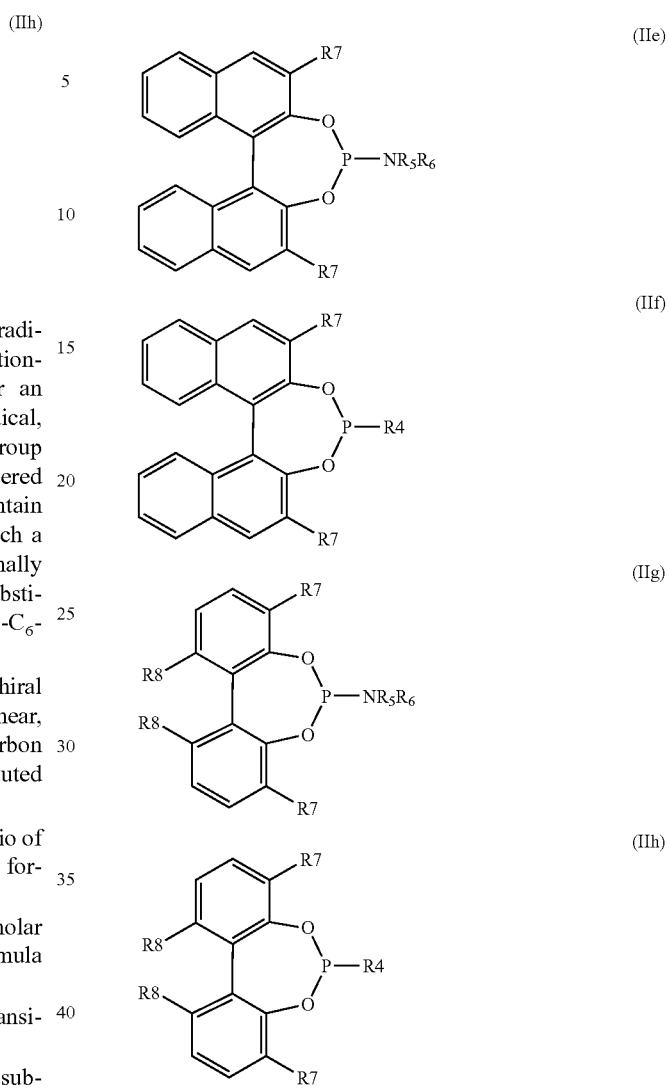

in which R4 is an optionally substituted $C_1$-$C_6$- alkyl radical, an optionally substituted phenyl radical or an optionally phenyl-substituted $C_1$-$C_6$- alkoxy radical, $R_5$ and $R_6$ are each independently a $C_1$-$C_6$-alkyl group or, together with the nitrogen atom, form a 5-membered or 6-membered ring which may optionally also contain an oxygen or sulfur atom, and R7 and R8 are each a linear or branched $C_1$-$C_6$-alkyl radical.

18. The catalyst system as claimed in claim 17, wherein the transition metal used is ruthenium, rhodium or iridium.

19. The catalyst system as claimed in claim 17, wherein the molar ratio of chiral ligand to achiral ligand is from 2.5:1 to 1.2:1.

20. A catalyst system for asymmetric transition metal catalysis, which comprises a transition metal from group VIII, IX or X and a combination of a chiral phosphorus ligand of the formula (IIa), (IIb), (IIc) or (IId)

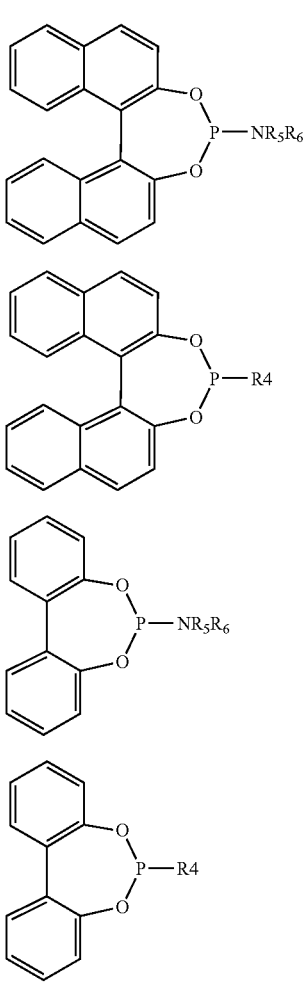

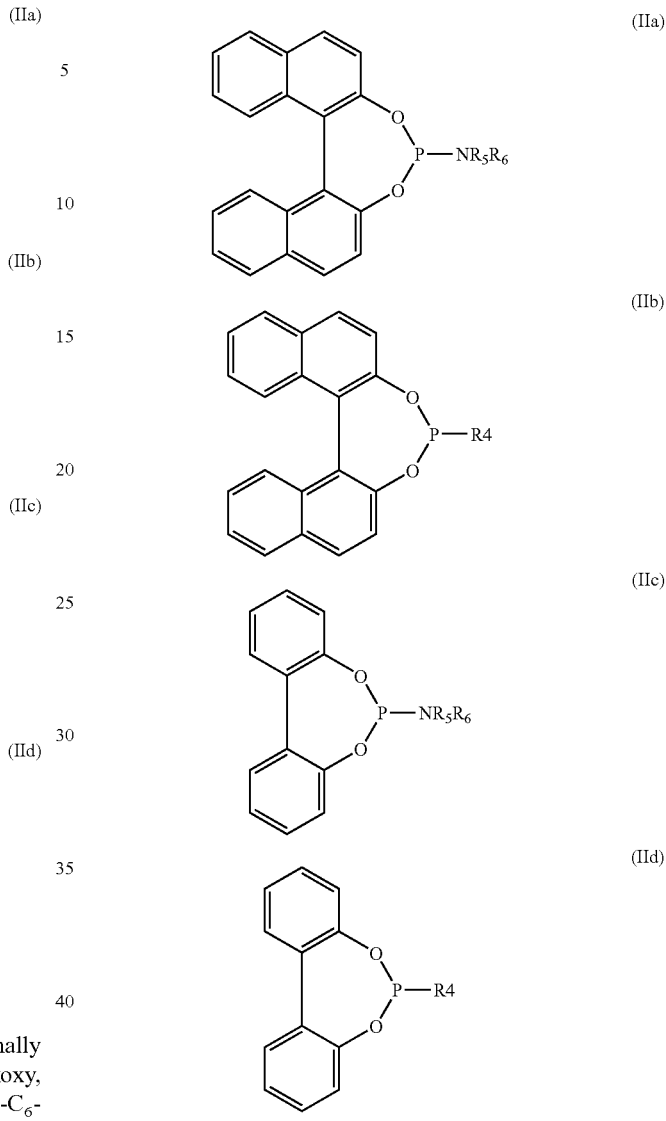

where the naphthyl and the phenyl groups may optionally be mono- or polysubstituted by halogen, alkyl, alkoxy, aryl or aryloxy, R4 is an optionally substituted $C_1$-$C_6$-alkyl radical, an optionally substituted phenyl radical, an optionally phenyl-substituted $C_1$-$C_8$-alkoxy radical or an optionally $C_1$-$C_6$-alkyl-substituted phenyloxy radical, and R5 and R6 are each independently a phenyl-substituted alkyl group having 1-6 carbon atoms or, together with the nitrogen atom, form a ring, and an achiral phosphine ligand of the formula (III)

P(R)$_3$ in which R is an optionally substituted alkyl or aryl radical, and wherein the molar ratio of chiral ligand to achiral ligand is from 2.5:1 to 1.2:1.

21. The catalyst system as claimed in claim 20, wherein the transition metal is ruthenium, rhodium or iridium.

22. A process for the transition metal-catalyzed asymmetric hydrogenation of unsaturated compounds which comprises subjecting the unsaturated compounds to transition metal-catalyzed asymmetric hydrogenation conditions in the presence of a catalyst system which comprises a transition metal from group VIII, IX or X and a combination of a chiral phosphorus ligand of the formula (IIa), (IIb), (IIc) or (IId)

where the naphthyl and the phenyl groups may optionally be mono- or polysubstituted by halogen, alkyl, alkoxy, aryl or aryloxy, R4 is an optionally substituted $C_1$-$C_6$-alkyl radical, an optionally substituted phenyl radical, an optionally phenyl-substituted $C_1$-$C_8$-alkoxy radical or an optionally $C_1$-$C_6$-alkyl-substituted phenyloxy radical, and R5 and R6 are each independently a phenyl-substituted alkyl group having 1-6 carbon atoms or, together with the nitrogen atom, form a ring, and an achiral phosphine ligand of the formula (III)

P(R)$_3$ in which R is an optionally substituted alkyl or aryl radical, and wherein the molar ratio of chiral ligand to achiral ligand is from 2.5:1 to 1.2:1.

23. The process as claimed in claim 22, wherein the transition metal is ruthenium, rhodium or iridium.

24. The process as claimed in claim 22, wherein the chiral ligand is a ligand of the formula (IIe), (IIf), (IIg) or (IIh)

(IIe)
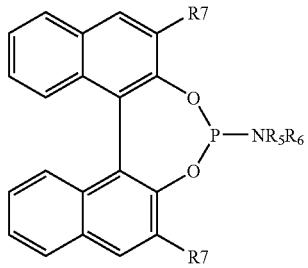

(IIf)
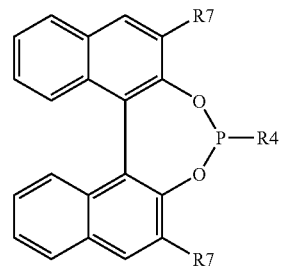

(IIg)
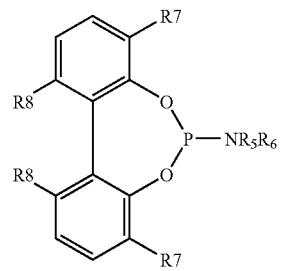

(IIh)
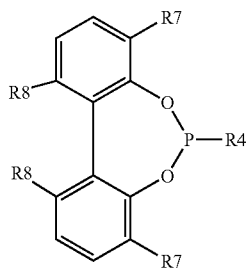

in which R4 is an optionally substituted $C_1$-$C_6$- alkyl radical, an optionally substituted phenyl radical or an optionally phenyl-substituted $C_1$-$C_6$- alkoxy radical, R5 and R6 are each independently a $C_1$-$C_6$-alkyl group or, together with the nitrogen atom, form a 5-membered or 6-membered ring which may optionally also contain an oxygen or sulfur atom, and R7 and R8 are each a linear or branched $C_1$-$C_6$-alkyl radical.

25. The process as claimed in claim 22, wherein the unsaturated compounds are acrylic acid derivatives of the formula (I)

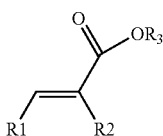

in which R1 is H or an optionally substituted $C_1$-$C_{20}$-alkyl, $C_5$-$C_{20}$-aryl or $C_5$-$C_{20}$- heteroaryl radical, R2 is an optionally substituted $C_1$-$C_{20}$-alkyl, $C_5$-$C_{20}$-aryl or $C_5$-$C_{20}$- heteroaryl radical, and R3 is H or a $C_1$-$C_6$-alkyl radical.

* * * * *